(12) United States Patent
Yu

(10) Patent No.: US 12,007,378 B2
(45) Date of Patent: Jun. 11, 2024

(54) SOIL TESTING DEVICE

(71) Applicant: Jian Yu, Shenzhen (CN)

(72) Inventor: Jian Yu, Shenzhen (CN)

( * ) Notice: Subject to any disclaimer, the term of this patent is extended or adjusted under 35 U.S.C. 154(b) by 0 days.

(21) Appl. No.: 18/237,395

(22) Filed: Aug. 23, 2023

(65) Prior Publication Data

US 2024/0053321 A1 Feb. 15, 2024

Related U.S. Application Data

(63) Continuation-in-part of application No. 17/887,502, filed on Aug. 14, 2022.

(51) Int. Cl.
| | |
|---|---|
| *G01R 27/08* | (2006.01) |
| *G01N 27/02* | (2006.01) |
| *G01N 27/04* | (2006.01) |
| *G01N 27/12* | (2006.01) |
| *G01N 33/24* | (2006.01) |
| *A01G 2/00* | (2018.01) |
| *A01G 25/16* | (2006.01) |
| *A01G 27/00* | (2006.01) |

(52) U.S. Cl.
CPC ........... *G01N 33/24* (2013.01); *G01N 27/025* (2013.01); *G01N 27/048* (2013.01); *G01N 27/121* (2013.01); *G01N 33/246* (2013.01); *A01G 2/00* (2018.02); *A01G 25/167* (2013.01); *A01G 27/005* (2013.01); *G01N 2033/245* (2013.01)

(58) Field of Classification Search
CPC ................. G01N 33/24; G01N 27/025; G01N 2033/245; G01N 27/048; G01N 27/121; G01N 33/246; A01G 25/167; A01G 2/00; A01G 27/005
USPC ......................................................... 324/696
See application file for complete search history.

(56) References Cited

U.S. PATENT DOCUMENTS

| | | | |
|---|---|---|---|
| 2015/0087072 A1* | 3/2015 | Adamchuk | G01N 33/24 422/68.1 |
| 2018/0239044 A1* | 8/2018 | Rhodes | G01N 27/043 |
| 2019/0310238 A1* | 10/2019 | Komatsu | G01N 27/72 |
| 2020/0390025 A1* | 12/2020 | Schoeny | A01C 5/066 |
| 2021/0123836 A1* | 4/2021 | Swanson | G01N 33/24 |
| 2021/0293985 A1* | 9/2021 | Kiss | G01K 13/00 |

* cited by examiner

*Primary Examiner* — Raul J Rios Russo

(57) ABSTRACT

A soil testing device includes a housing, a display unit, and at least one sensor assembly. The display unit is disposed on the housing. The at least one sensor assembly is rotatably connected to the housing, and the at least one sensor assembly is electrically connected to the display unit. The at least one sensor assembly is configured to insert into soil and output an electrical signal corresponding to a soil parameter, and the display unit is configured to display a value of the soil parameter corresponding to the electrical signal output by the at least one sensor assembly.

18 Claims, 8 Drawing Sheets

SOIL TESTING DEVICE

TECHNICAL FIELD

The present disclosure relates to a technical field of electronic gardening tools, and in particular to a soil testing device.

BACKGROUND

Soil testing devices are configured to measure characteristic parameters of soil, such as one or more of fertility degree, moisture content, and hydrogen ion concentration index (PH). The soil testing devices in the prior art are not flexible enough in structure, which is inconvenient for use.

SUMMARY

In one aspect of the present disclosure, a soil testing device includes a housing, a display unit, and at least one sensor assembly. The display unit is disposed on the housing. The at least one sensor assembly is rotatably connected to the housing, and electrically connected to the display unit. The at least one sensor assembly is configured to insert into soil and output an electrical signal corresponding to a soil parameter, and the display unit is configured to display a value of the soil parameter corresponding to the electrical signal output by the at least one sensor assembly.

BRIEF DESCRIPTION OF DRAWINGS

In order to more clearly illustrate technical solutions in embodiments of the present disclosure, accompanying drawings that need to be used in description of the embodiments are briefly described below. Obviously, the accompanying drawings in the following description are merely some embodiments of the present disclosure, and for those skilled in the art, other drawings may be obtained according to these drawings without involving any inventive effort.

For a more complete understanding of the present disclosure and beneficial effects thereof, the following description is made below in conjunction with the accompanying drawings, in which same reference numerals refer to same parts in the following description.

Figure 1:
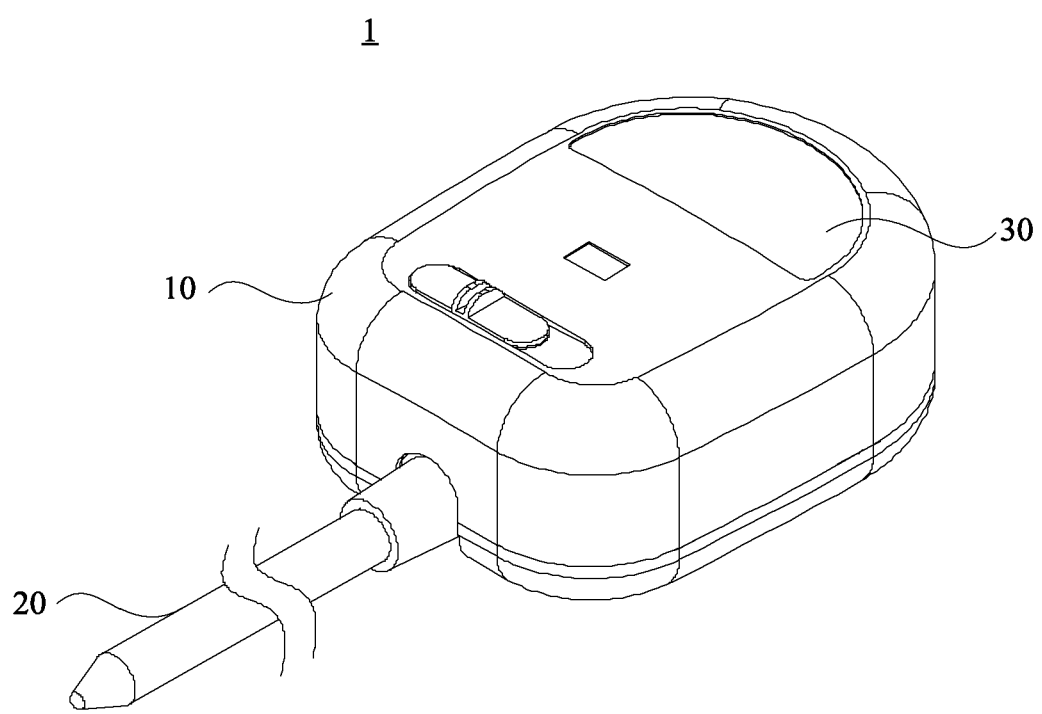
FIG. 1 is a structural schematic diagram of a soil testing device according to one embodiment of the present disclosure.

Reference numerals in the drawings: 1. soil testing device; 10. housing; 11. rotating space; 12. upper housing; 121. first limiting groove; 122. first bottom wall; 124. first side wall; 126. first arc-shaped plate; 14. lower housing; 141. second limiting groove; 142. first bottom plate; 1421. second limiting opening; 144. first side plate; 1441. first limiting opening; 146. baffle; 1461. third limiting opening; 147. second bottom wall; 1471. fourth limiting opening; 148. second side wall; 1481. fifth limiting opening; 149. second arc-shaped plate; 15. accommodating space; 16. bracket; 162. first cover portion; 1622. first portion; 1623. slit; 1624. second portion; 164. second cover portion; 166. third cover portion; 18. second limiting structure; 182. inner gear structure; 184. limiting protrusion block; 20. sensor assembly; 22. rotating portion; 222. base body; 224. connecting column; 226. protruding column; 24. detecting rod; 26. first limiting structure; 262. outer gear structure; 263. limiting notch; 28. rotating body; 282. first side; 30. display unit; 40. circuit board.

DETAILED DESCRIPTION

Technical solutions in embodiments of the present disclosure are clearly and completely described below with reference to accompanying drawings in the embodiments of the present disclosure. Obviously, the described embodiments are only a part of the embodiments of the present disclosure, but are not all embodiments. All other embodiments obtained those who skilled in the art based on the embodiments of the present disclosure without creative efforts shall fall within protection scopes of the present disclosure.

Figure 2:
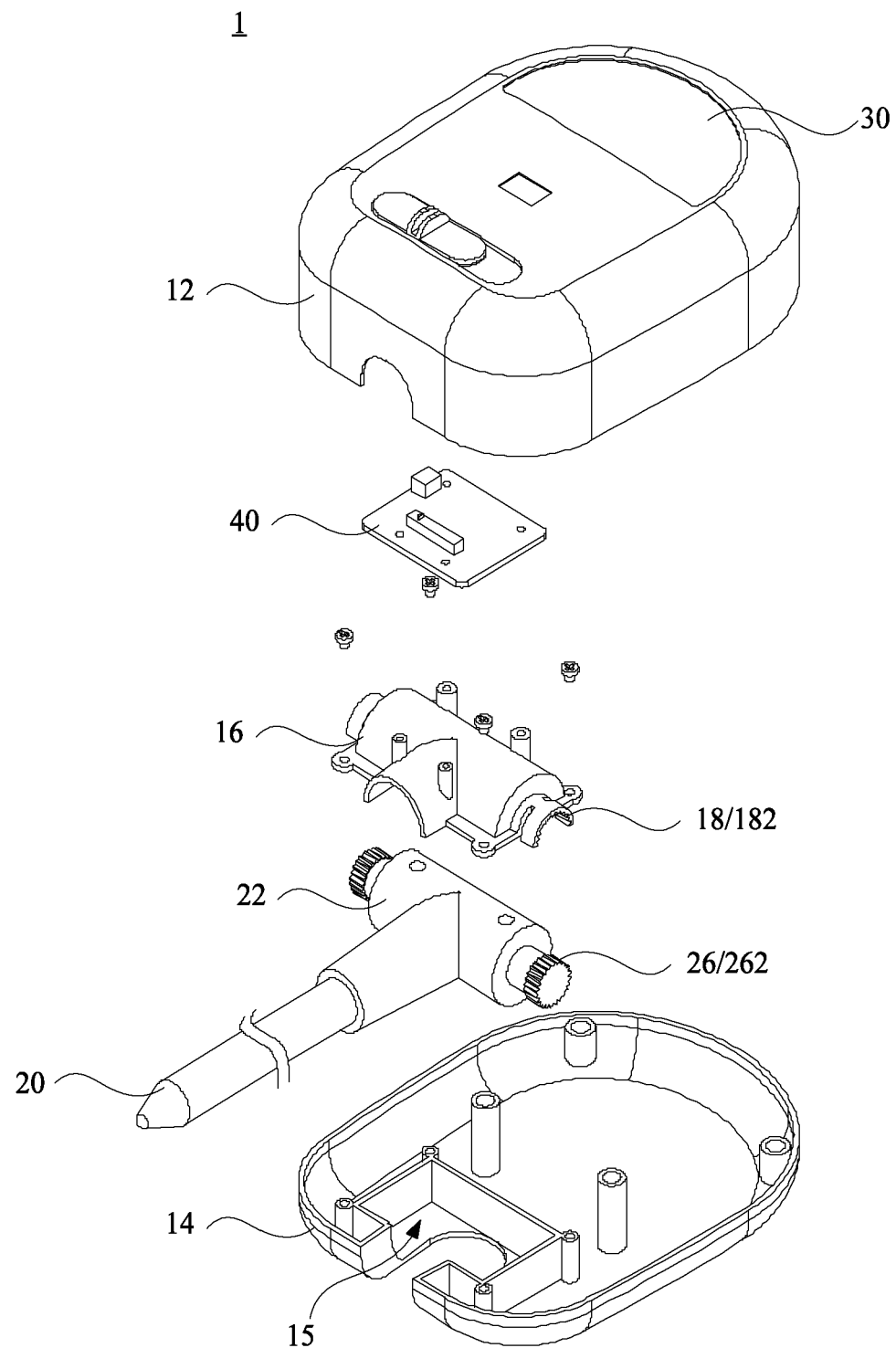
FIG. 2 is an exploded schematic diagram of the soil testing device shown in FIG. 1.

The present disclosure provides a soil testing device, please refer to FIGS. 1 and 2, FIG. 1 is a structural schematic diagram of a soil testing device according to one embodiment of the present disclosure, and FIG. 2 is an exploded schematic diagram of the soil testing device shown in FIG. 1. The soil testing device 1 includes a housing 10, a display unit 30, and at least one sensor assembly 20. The display unit 30 is disposed on the housing 10. The at least one sensor assembly 20 is rotatably connected to the housing 10, and electrically connected to the display unit 30. The at least one sensor assembly 20 is configured to insert into soil and output an electrical signal corresponding to a soil parameter, and the display unit 30 is configured to display a value of the soil parameter corresponding to the electrical signal output by the at least one sensor assembly 20.

The at least one sensor assembly 20 and the display unit 30 cooperate to measure the soil parameter and display the value of the soil parameter, the soil parameter corresponding to the electrical signal is selected from soil parameter including values of fertility degree, moisture content, hydrogen ion concentration index (PH), etc., the display unit is configured to display the value of the soil parameter corresponding to the values of the fertility degree, the moisture content, the PH, or other parameters of soil being detected, which is convenient for users to quickly obtain the value of the soil parameter to be measured outdoors. After the at least one sensor assembly 20 is inserted into the soil, the housing 10 is rotatable relative to the at least one sensor assembly 20 to be at a suitable angle with respect to the at least one sensor assembly 20, which is flexible in structure, thereby being convenient to view the display unit disposed on the housing. Moreover, the at least one sensor assembly 20 may insert into the soil after the at least one sensor assembly 20 is rotated at a certain angle relative to the housing 10. Alternatively, a force is applied on the housing 10 for conveniently inserting the at least one sensor assembly 20 into the soil.

For better understanding structures of the at least one sensor assembly 20 and the display unit 30, the at least one sensor assembly 20 and the display unit 30 are described in detail below.

In some embodiments, the at least one sensor assembly 20 includes a sensor and a sensor probe. After the sensor is inserted into the soil, the sensor, the sensor probe, and the soil jointly form a battery cell. It is understood that the sensor can generate different electrical signals, such as currents, according to different levels of the PH, the moisture content, and the fertility degree of the soil.

In some embodiments, the sensor is made of metal, such as aluminum, aluminum alloy, copper, copper alloy, other metal materials, or other metal alloy materials.

In some embodiments, the sensor probe is made of metal, such as aluminum, aluminum alloy, copper, copper alloy, other metal materials, or other metal alloy materials.

In some embodiments, the at least one sensor assembly 20 is a PH sensor assembly 20 for measuring a PH value of the soil, a moisture content sensor assembly 20 for measuring a moisture content value of the soil, or a fertility degree sensor assembly 20 for measuring a fertility degree value of the soil. Specifically, the PH sensor assembly 20 includes a PH sensor and a PH sensor probe, the moisture content sensor assembly 20 includes a moisture content sensor and a moisture content sensor probe, and the fertility degree sensor assembly 20 includes a fertility degree sensor and a fertility degree sensor probe.

In some embodiments, the soil testing device 1 includes one sensor assembly 20, two sensor assemblies 20, three sensor assemblies 20, or more sensor assemblies 20, the number of the at least one sensor assembly 20 may be set according to requirements, and the at least one sensor assembly 20 may include at least one of the PH sensor assembly 20, the moisture content sensor assembly 20, and the fertility degree sensor assembly 20.

In some embodiments, after the at least one sensor assembly 20 is inserted into the soil, the at least one sensor assembly 20 and the soil jointly form the battery cell. The at least one sensor assembly 20 transmits the electrical signal, such as a micro-current, of the battery cell to the display unit 30, and the display unit 30 displays the value reflecting the soil parameter corresponding to the electrical signal, such as the micro-current.

In some embodiments, after the at least one sensor assembly 20 is inserted into the soil, an electric signal is applied to the at least one sensor assembly 20, so that the sensor, the soil, and the sensor probe are electrically connected and form a circuit loop (i.e., the battery cell). Since soil parameters of different soil are different, for example, the different soil has different PH values, different moisture content values, or different fertility values, impedances corresponding to different soil are different, causing changes of the current or the voltage in the circuit loop. The current or the voltage output by the circuit loop is the electrical signal corresponding to the soil parameter, and the display unit 30 may display the value reflecting the soil parameter according to the electrical signal. In some embodiments, the display unit 30 is connected in series with the sensor, the soil, and the sensor probe, so as to display value reflecting the soil parameter according to the current in the circuit loop. In some other embodiments, the display unit 30 is connected in parallel with the sensor, the soil, and the sensor probe to display the value reflecting the soil parameter according to the voltage of the circuit loop.

In some embodiments, the display unit 30 includes an analog meter, and the analog meter is electrically connected to the at least one sensor assembly 20. The at least one sensor assembly 20 transmits the electrical signal to the analog meter, and the analog meter displays the value reflecting the soil parameter. The value of the soil parameter is displayed on the analog meter without additional calibration.

In some embodiments, the display unit 30 includes a digital meter, and the digital meter is electrically connected to the at least one sensor assembly 20. The at least one sensor assembly 20 transmits the electrical signal to the digital meter, the digital meter converts the electrical signal into a corresponding digital signal, and the corresponding digital signal displays the value reflecting the soil parameter.

In some embodiments, the at least one sensor assembly 20 further includes at least one first limiting structure 26, the housing 10 further includes at least one second limiting structure 18, and the at least one first limiting structure 26 is matched with the at least one second limiting structure 18, so as to limit the at least one sensor assembly 20 in a predetermined position of the housing 10. The at least one sensor assembly 20 may be limited at a certain angle with the housing 10 as required by the at least one first limiting structure 26 and the at least one second limiting structure 18, which is convenient for the users to use. For example, after the at least one sensor assembly 20 is fixed at the certain angle with the housing 10, the users are able to view the display unit 30 disposed on the housing 10 without assistant, which is convenient.

In some embodiments, the at least one first limiting structure 26 includes an outer gear structure 262, the at least one second limiting structure 18 includes an inner gear structure 182 corresponding to the outer gear structure 262, and the outer gear structure 262 is engaged with the inner gear structure 182. The outer gear structure 262 and the inner gear structure 182 limit the at least one sensor assembly 20 and the housing 10. It should be understood that, in some examples, when the at least one sensor assembly 20 rotates relative to the housing 10, the outer gear structure 262 rotates along with the at least one sensor assembly 20, and the inner gear structure 182 is stationary. If one of gear teeth of the outer gear structure 262 is located on a corresponding one of ridges of the inner gear structure 182, the ridges of the inner gear structure 182 have a relatively large resistance to the gear teeth of the outer gear structure 262, so as to limit the outer gear structure 262, that is, the at least one sensor assembly 20 is limited at a position of the housing 10 where the at least one sensor assembly 20 is currently located.

It should be understood that, in some embodiments, the gear teeth of the outer gear structure 262 have elasticity, and when the outer gear structure 262 rotates, the ridges of the inner gear structure 182 have a large resistance to the gear teeth of the outer gear structure 262, and if the gear teeth of the outer gear structure 262 have large driving power, the gear teeth of the outer gear structure 262 are elastically deformed to overcome the large resistance from the ridges of the inner gear structure to rotate the outer gear structure 262 relative to the inner gear structure 182. The resistance from the ridges of the inner gear structure 182 to the gear teeth of the outer gear structure 262 is determined according to an elastic deformation force of each of the gear teeth of the outer gear structure 262, the larger the elastic deformation force is, the greater the corresponding resistance is, and the smaller the elastic deformation force is, the smaller the corresponding resistance is. A structure of each of the gear teeth and a material of each of the gear teeth may be set according to requirements, so as to obtain suitable resistance between the inner gear structure 182 and the outer gear structure 262.

In some other embodiments, the ridges of the inner gear structure 182 have elasticity, and when the outer gear structure 262 rotates, the ridges of the inner gear structure 182 have the large resistance to the gear teeth of the outer gear structure 262, and if the gear teeth of the outer gear structure 262 have the large driving power, the ridges of the inner gear structure 182 are elastically deformed to overcome the large resistance from the ridges of the inner gear structure to rotate the outer gear structure 262 relative to the inner gear structure 182. The resistance from the ridges of the inner gear structure 182 to the gear teeth of the outer gear structure 262 may be determined according to an elastic deformation force of the ridges of the inner gear structure 182, the larger the elastic deformation force is, the greater the corresponding resistance is, and the smaller the elastic deformation force is, the smaller the corresponding resistance is, and a structure of each of the ridges and a material of each of the ridges may be set according to requirements, so as to obtain suitable resistance between the inner gear structure 182 and the outer gear structure 262.

Figure 3:
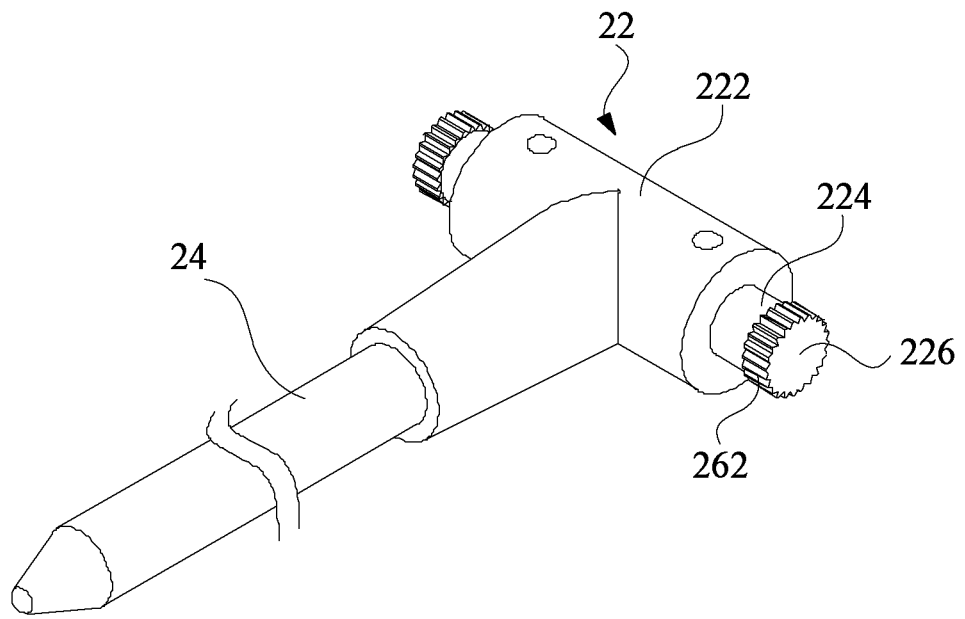
FIG. 3 is a structural schematic diagram of one senor assembly in the soil testing device shown in FIG. 1.

Please further refer to FIG. 3, FIG. 3 is a structural schematic diagram of one senor assembly of the soil testing device shown in FIG. 1. In some embodiments, the at least one sensor assembly 20 includes a rotating portion 22 and a detecting rod 24, the rotating portion 22 is connected with the detecting rod 24, the rotating portion 22 is disposed in the housing 10, and the detecting rod 24 extends out of the housing 10 from an interior of the housing 10. It should be understood that the detecting rod 24 is configured to insert into the soil, and both the sensor and the sensor probe are disposed in the detecting rod 24.

The rotating portion 22 includes a base body 222 and two protruding columns 226, the two protruding columns 226 protrude from two sides of the base body 222 in a direction perpendicular to an extending direction of the detecting rod 24, and the outer gear structure 262 is disposed on a periphery of a corresponding one of the two protruding columns 226. The two protruding columns 226 are disposed at the two sides of the base body 222 to achieve limitation, the base body 222 is configured to achieve a rotating function of the at least one sensor assembly 20, the two protruding columns 226 and the outer gear structure 262 disposed on a corresponding one of the two protruding columns 226 are configured to achieve a limiting function of the at least one sensor assembly 20, and a limiting effect is achieved only through small structural improvement. Moreover, the two protruding columns 226 are disposed at an outermost side of the rotating portion 22, which are convenient for setting of the outer gear structure 262.

In some embodiments, the two protruding columns 226 and the base body 222 are columnar, and a diameter of each of the two protruding columns 226 is much less than a diameter of the base body 222, and providing the outer gear structure 262 on the corresponding one of the two protruding columns 226 puts the outer gear structure 262 in smaller size and lower cost than providing the outer gear structure 262 on the base body 222.

Figure 4:
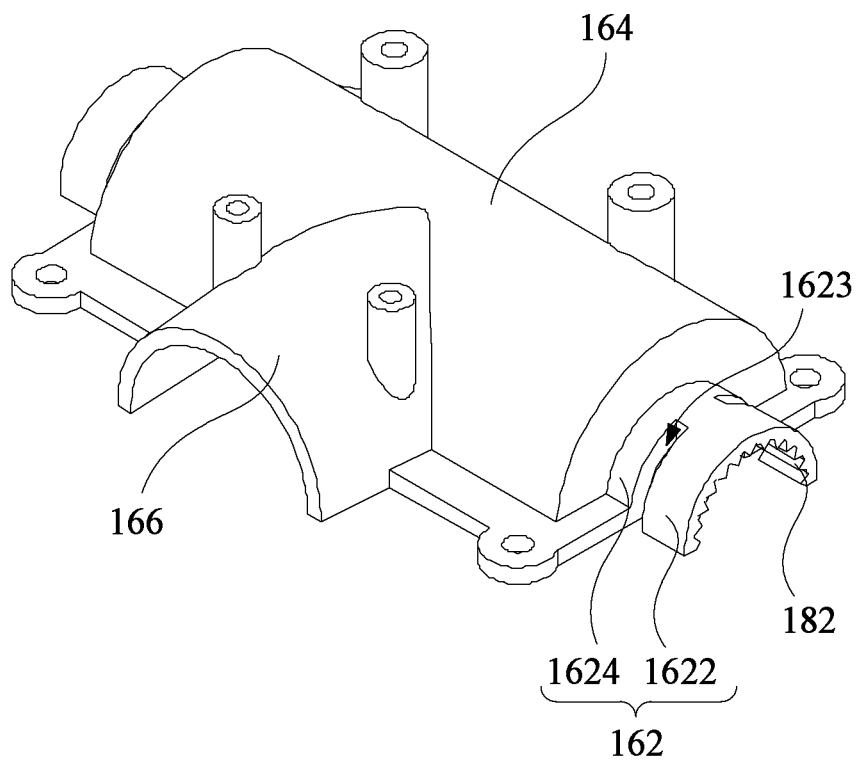
FIG. 4 is a structural schematic diagram of a bracket of the soil testing device shown in FIG. 1.

Please further refer to FIGS. 2 and 4, FIG. 4 is a structural schematic diagram of a bracket of the soil testing device shown in FIG. 1. In some embodiments, the housing 10 includes an upper housing 12, a lower housing 14, and a bracket 16. The upper housing 12 is fixedly connected to the lower housing 14, the bracket 16 is disposed between the upper housing 12 and the lower housing 14, the bracket 16 and the lower housing 14 are spaced apart to form an accommodating space 15, and the rotating portion 22 is disposed in the accommodating space 15 and is rotatable in the accommodating space 15. The bracket 16 includes at least one first cover portion 162, the at least one first cover portion 162 covers on a part of the at least one first limiting structure 26, and the inner gear structure 182 is disposed at one side, facing the at least one first limiting structure 26, of the at least one first cover portion 162.

The at least one first cover portion 162 does not need to cover a whole body of the at least one first limiting structure 26, that is, the at least one first cover portion 162 does not need to cover a whole body of the outer gear structure 262, which is beneficial for design and production of a structure of the soil testing device 1, is convenient to assemble the soil testing device 1, and is low in production and assembly costs. The outer gear structure 262 is a circular gear structure, the part of the outer gear structure 262 covered by the at least one first cover portion 162 may occupy ⅓ to ⅔ of a whole body of the outer gear structure 262. Alternatively, in some examples, the at least one first cover portion 162 covers a half of the outer gear structure 262. In some examples, the at least one first cover portion 162 is arc-shaped.

In some embodiments, the bracket 16 further includes a second cover portion 164 and a third cover portion 166, the second cover portion 164 is connected with the third cover portion 166, the second cover portion 164 covers on the base body 222, and the third cover portion 166 covers on a part of the detecting rod 24. The second cover portion 164 and the lower housing 14 cooperate to limit the base body 222, and the third cover portion 166 covers on the part of the detecting rod 24 to limit and protect the detecting rod 24. In some examples, the second cover portion 164 and the third cover portion 166 are arc-shaped. Two first cover portions 164 are provided, the two first cover portions 164 are disposed at two sides of the second cover portion 164 in the direction perpendicular to the extending direction of the detecting rod 24. Two inner gear structure 182 are provided, and the two inner gear structures 182 are respectively disposed on the two first cover portions. The two inner gear structure 182 disposed on two sides of the second cover portion 164 limits the at least one sensor assembly 20 from two sides thereof, so the at least one sensor assembly 20 is balanced. Moreover, the at least one sensor assembly is prevented from inclining due to single-side limitation, and a limiting effect of which is better.

Figure 5:
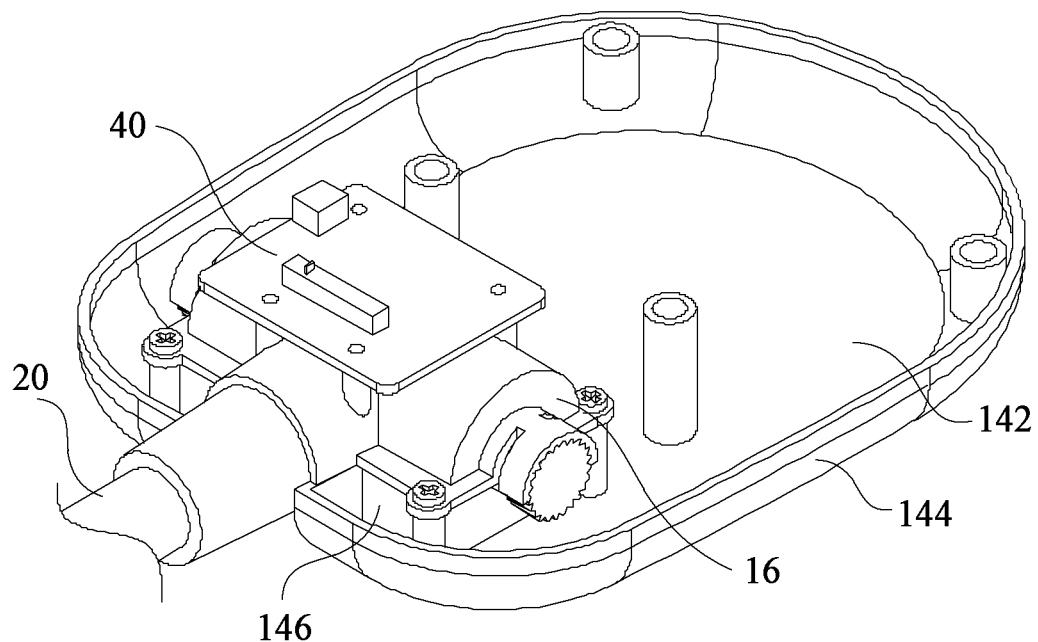
FIG. 5 is a structural schematic diagram of partial structures of the soil testing device shown in FIG. 1.

Please further refer to FIGS. 3-5, FIG. 5 is a structural schematic diagram of partial structures of the soil testing device shown in FIG. 1. In some embodiments, the rotating portion 22 further includes two connecting columns 224, each of the two connecting columns 224 is disposed between the base body 222 and a corresponding one of the two protruding columns 26. Each of the two first cover portions 162 includes a first portion 1622 and a second portion 1624, the first portion 1622 is connected with the second portion 1624, a slit 1623 is defined between the first portion 1622 and the second portion 1624, the first portion 1622 covers on the outer gear structure 262, and the second portion 1624 covers on a part of a correspondingly one of the two connecting columns 224. That is, the two first cover portions 162 include two first portions 1622 and two second portions 1624, the two first cover portions 162 are respectively connected with the two second portions, two slits 1623 are respectively defined between the two first portions 1622 and the two second portions 1624, each of the two first portions 1622 covers a corresponding outer gear structure 262, and the two second portions 1624 respectively cover on parts of the two connecting columns 224. Components below the two first cover portions 162 are seen through the two slits 1623, so as to determine whether each of the two first portions 1622 covers a corresponding outer gear structure 262.

Figure 6:
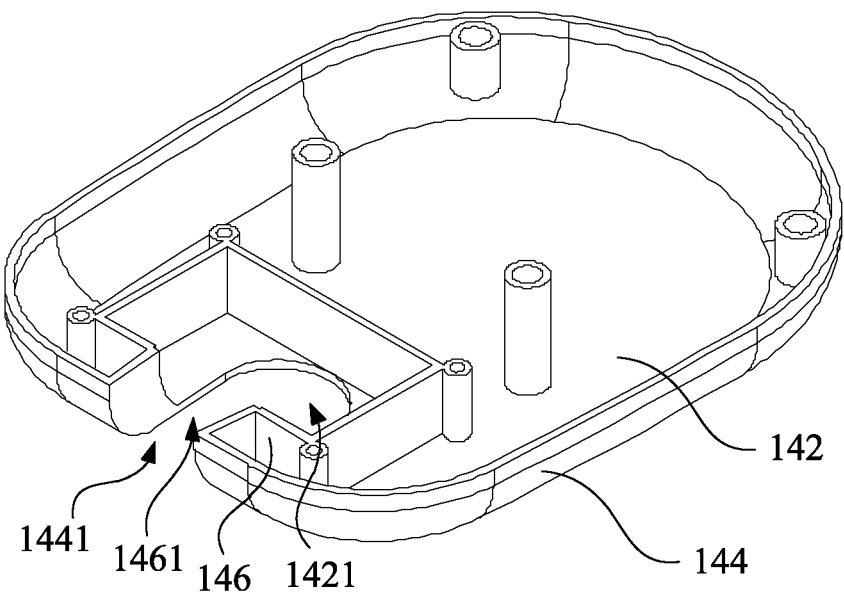
FIG. 6 is a structural schematic diagram of a lower housing of the soil testing device shown in FIG. 1.

Please refer to FIG. 6, FIG. 6 is a structural schematic diagram of a lower housing in the soil testing device shown in FIG. 1. In some embodiments, the lower housing 14 includes a first bottom plate 142 and a first side plate 144, and the first side plate 144 is disposed around an edge of the first bottom plate 142 and is disposed at one side, facing the upper housing 12, of the first bottom plate 142. That is, the first side plate 144 is disposed around the edge of the first bottom plate 142 and forms a groove structure with the first bottom plate 142. A first limiting opening 1441 for allowing rotation of the detecting rod 24 is defined on the first side plate 144, a second limiting opening 1421 for allowing the rotation of the detecting rod 24 is defined on the first bottom plate 142, and the first limiting opening 1441 is communicated with the second limiting opening 1421. The second limiting opening 1421 and the first limiting opening 1441 facilitate the rotation of the detecting rod 24 and define a rotating direction of the detecting rod 24. The upper housing 12 is not provided with a limiting opening, so that the detecting rod 24 only rotates toward the lower housing 14.

In some embodiments, the lower housing 14 further includes a baffle 146, and the baffle 146 is disposed at the one side, facing the upper housing 12, of the bottom plate 142. The baffle 146 is disposed around the rotating portion 22 and forms an accommodating groove with the bottom plate 142 for accommodating the rotating portion 22. A third limiting opening 1461 for allowing the rotation of the detecting rod 24 is defined on the baffle 146. The third limiting opening 1461, the second limiting opening 1421, and the first limiting opening 1441 are communicated. The baffle 146 is disposed around the rotating portion 22.

In some other embodiments, the upper housing 12 is provided with the limiting opening, and the detecting rod 24 is rotatable toward the upper housing 12.

In some embodiments, the bracket 16 covers on the rotating portion 22 and is fixedly connected to the baffle 146, so as to limit the rotating portion 22 between the bracket 16 and the lower housing 14. The baffle 146 not only limits the rotating portion 22 in a first direction, such as a horizontal direction, but is also fixedly connected to the bracket 16, so as to cooperate with the first bottom plate 142 to limit the rotating portion 22 in a second direction, such as a vertical direction.

In some embodiments, the soil testing device 1 further includes a circuit board 40, and the circuit board 40 is disposed at one side of the bracket 16 facing away from the lower housing. A first through hole (not shown in the drawings) is defined on the bracket 16, at least one wire passes through the first through hole, and the circuit board 40 is electrically connected to the at least one sensor assembly 20 through the at least one wire, which is convenient for electrically connecting the circuit board 40 to the at least one sensor assembly 20.

In some embodiments, a control switch is disposed on the circuit board 40, a switch opening corresponding to the control switch is defined on the upper housing 12, and the control switch is partially exposed out of the switch opening, so the control switch is able to be operated by the users. The control switch may be set according to requirements, for example, the control switch may be a toggle switch or a knob switch, etc. Functions of the control switch may be set according to requirements, for example, the control switch controls the at least one sensor assembly to power on or off, or when a plurality of sensor assemblies are provided, the control switch controls one or more of the plurality of sensor assemblies to work.

In some embodiment, the soil testing device 1 includes the plurality of the sensor assemblies 20, each of the plurality of the sensor assemblies 20 includes one rotating portion 22 and one detecting rod 24. In other embodiments, the soil testing device 1 includes the plurality of the sensor assemblies 20, and the plurality of the sensor assemblies 20 share one rotating portion 22.

Figure 7:
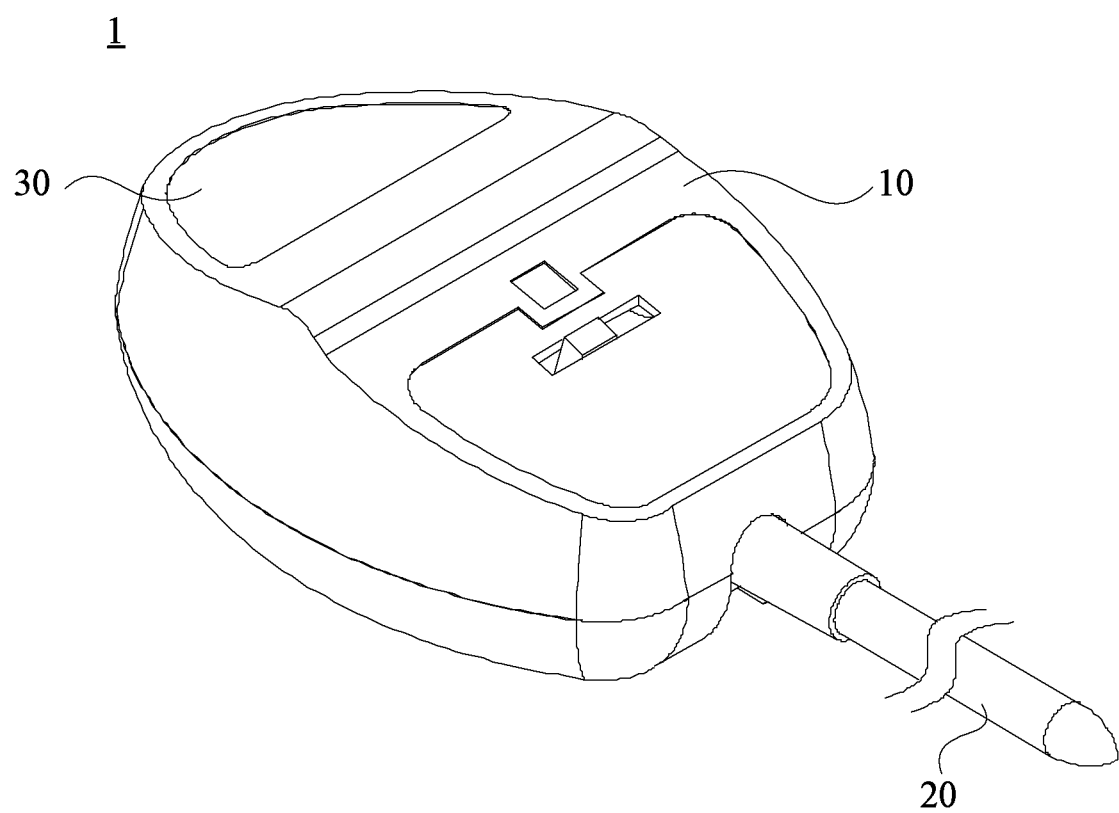
FIG. 7 is another structural schematic diagram of the soil testing device according to one embodiment of the present disclosure.
Figure 8:
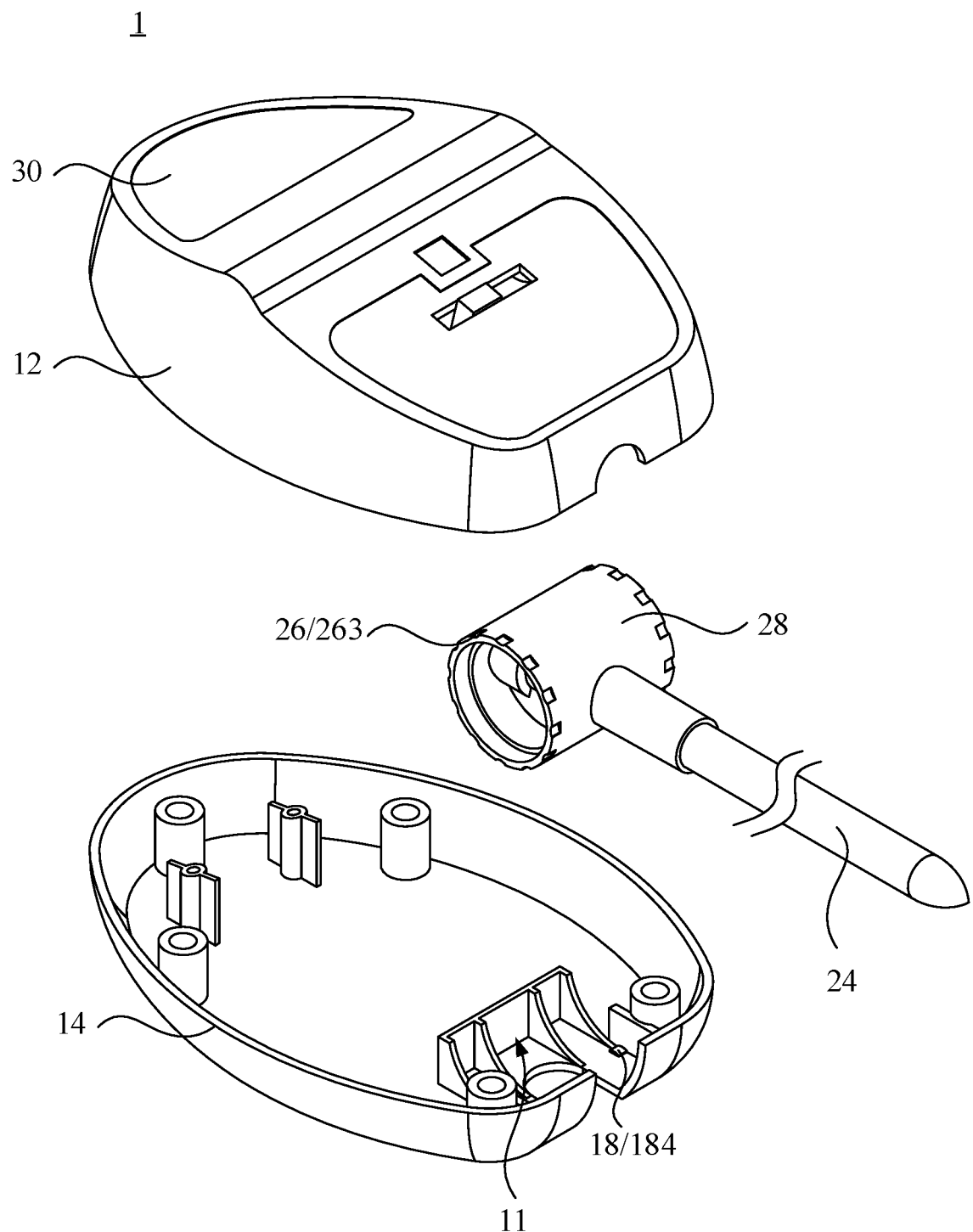
FIG. 8 is an exploded schematic diagram of the soil testing device shown in FIG. 7.

Please refer to FIGS. 7 and 8, FIG. 7 is another structural schematic diagram of the soil testing device according to one embodiment of the present disclosure, and FIG. 8 is an exploded schematic diagram of the soil testing device shown in FIG. 7. In some embodiments, a rotating space 11 is defined in the housing 10, the at least one sensor assembly 10 includes a rotating body 28, the rotating body 28 is columnar and is disposed in the rotating space 11, and the rotating body 28 is capable of rotating in the rotating space 11. The at least one first limiting structure includes limiting notches 263, and the limiting notches 263 are defined on an outer peripheral surface of the rotating body 28 and defined around a circumference of the rotating body 28. The at least one second limiting structure includes at least one limiting protrusion block 184, the at least one limiting protrusion block 184 is disposed on the housing 10, and the at least one limiting protrusion block 184 is configured to engage with a corresponding one of the limiting notches 263, so as to limit the rotating body 28.

When the rotating body 28 rotates in the rotating space 11, if each of the limiting notches 263 on the rotating body 28 is engaged with the at least one limiting protrusion block 184, the at least one limiting protrusion block 184 generates a large resistance when the rotating body 28 rotates, so that the rotating body 28 is limited in a current position. That is, the at least one sensor assembly 20 is limited in a current position. If portions of the rotating body 28 except for the limiting notches 263 are in contact with the at least one limiting protrusion block 184, the at least one limiting protrusion block 184 does not generate the large resistance to the rotation of the rotating body 28, so that the rotation of rotating body 28 is basically not affected, that is, the rotation of the at least one sensor assembly 20 is not affected.

In some embodiments, a distance between any adjacent two of the limiting notches 263 is fixed. That is, the limiting notches 263 are uniformly defined at a first end portion or a second end portion. In some other embodiments, the distance between any adjacent two of the limiting notches 263 varies. For example, when the at least one sensor assembly 20 and the housing 10 extend in the same direction, distances between the limiting notches 263 gradually increase in a rotating direction of the rotating body 28. That is, a rotating angle of the rotating body 28 in an early rotating stage is relatively small, and the rotating angle of the rotating body 28 in a later rotating stage is relatively large, so that the rotating body 28 has high rotation precision in the early rotating stage. Alternatively, when the at least one sensor assembly 20 and the housing 10 extend in the same direction, the distances between the limiting notches 263 gradually decrease in the rotating direction of the rotating body 28. That is, the rotating angle of the rotating body 28 in the early rotating stage is relatively large, and the rotating angle of the rotating body 28 is relatively small in a later rotating stage, so that the rotating body 28 has high rotation precision in the later rotating stage.

Figure 9:
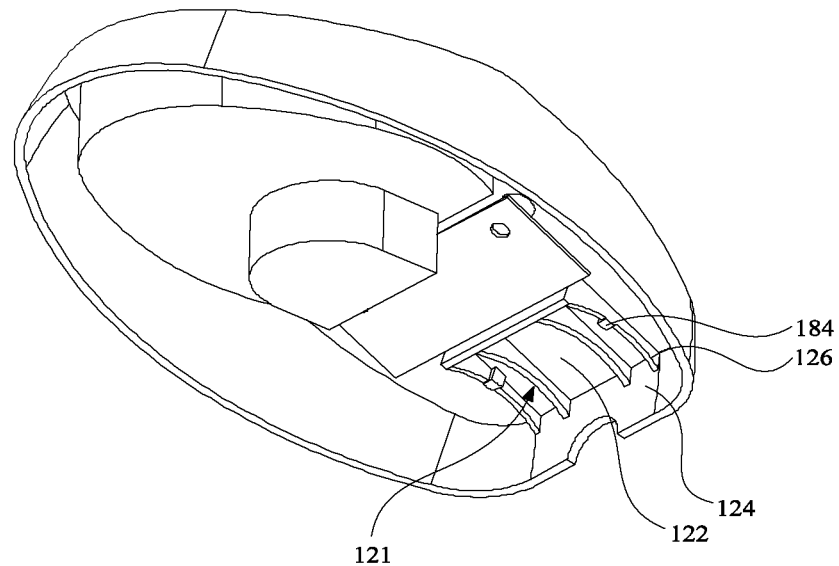
FIG. 9 is a structural schematic diagram of an upper housing of the soil testing device shown in FIG. 7.
Figure 10:
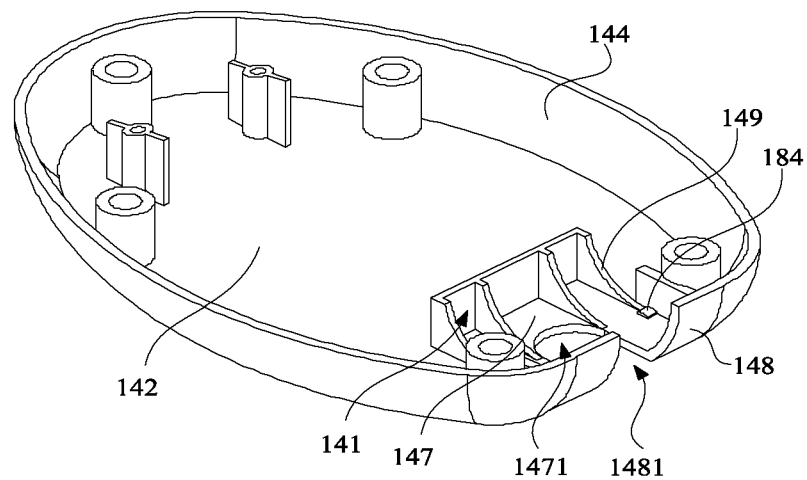
FIG. 10 is a structural schematic diagram of a lower housing of the soil testing device shown in FIG. 7.

Please refer to FIGS. 9 and 10, FIG. 9 is a structural schematic diagram of an upper housing of the soil testing device shown in FIG. 7, and FIG. 10 is a structural schematic diagram of a lower housing of the soil testing device shown in FIG. 7. In some embodiments, the housing 10 includes the upper housing 12 and the lower housing 14, at least one first limiting groove 121 is defined at one side, facing the lower housing 14, of the upper housing 12, at least one second limiting groove 141 is defined at one side, facing the upper housing 12, of the lower housing 14, and the at least one first limiting groove 121 and the at least one second limiting groove 141 are disposed opposite to each other and form the rotating space 11. The upper housing 12 and the lower housing 14 form the rotating space 11, so that a structure, such as the bracket 16, is not required, which is simple in structure and low in manufacturing cost.

In some embodiments, the rotating body 28 includes the first end portion and the second end portion, the first end portion and the second end portion are disposed along an axial direction of the rotating body 28, and the limiting notches 263 are defined around outer peripheral surfaces of the first end portion and the second end portion. One or more limiting protrusion blocks 184 are disposed on the housing 10 and are corresponding to the limiting notches 263 defined on the first end portion. Similarly, one or more limiting protrusion blocks 184 are disposed on the housing and are corresponding to the limiting notches 263 defined on the second end portion. In some examples, one or more limiting protrusion blocks 184 are disposed on the upper housing 12 and are corresponding to the limiting notches 263 defined on the first end portion, one or more limiting protrusion blocks 184 are disposed on the lower housing 14 and are corresponding to the limiting notches 263 defined on the first end portion, one or more limiting protrusion blocks 184 are disposed on the upper housing 12 and are corresponding to the limiting notches 263 defined on the second end portion, and one or more limiting protrusion blocks 184 are disposed on the lower housing 14 and are corresponding to the limiting notches 263 defined on the second end portion.

In some embodiments, the upper housing 12 includes a first bottom wall 122 and a first side wall 124. The first bottom wall 122 and the first side wall 124 form the at least one first limiting groove 121. The upper housing 12 further includes at least one first arc-shaped plate 126, and the at least one first arc-shaped plate 126 is disposed on the first bottom wall 122 and is connected to the first side wall 124. One side, away from the first bottom wall 122, of the at least one first arc-shaped plate 126 is an arc-shaped structure matched with the rotating body 28. The at least one first arc-shaped plate 126 is capable of being attached to the rotating body 28, so that the rotating body 28 is limited in the rotating space 11, meanwhile, the at least one first arc-shaped plate 126 also guides the rotation of the rotating body 28.

In some embodiments, the at least one limiting protrusion block 184 is disposed on the at least one first arc-shaped plate 126. The at least one first arc-shaped plate 126 extends along a first side of the rotating body 28 to a second side of the rotating body 28, that is, the at least one first arc-shaped plate 126 covers a third side, facing the upper housing 12, of the rotating body 28. In some embodiments, the at least one limiting protrusion block 184 is disposed on the at least one first arc-shaped plate 126 and is adjacent to the at least one first arc-shaped plate 126.

In some embodiments, the lower housing 14 includes a second bottom wall 147 and a second side wall 148. The second bottom wall 147 and the second side wall 148 form the at least one second limiting groove 141. The lower housing 14 further includes at least one second arc-shaped plate 149, and the at least one second arc-shaped plate 149 is disposed on the second bottom wall 147 and is connected to the second side wall 148. One side, away from the second bottom wall 147, of the at least one second arc-shaped plate 149 is an arc-shaped structure matched with the rotating body 28. The at least one second arc-shaped plate 149 is capable of being attached to the rotating body 28, so that the rotating body 28 is limited in the rotating space 11, meanwhile, the at least one second arc-shaped plate 149 also guides the rotation of the rotating body 28.

In some embodiments, the at least one limiting protrusion block 184 is disposed on the second bottom wall 147 and is adjacent to the at least one second arc-shaped plate 149.

In some embodiments, the at least one first arc-shaped plate 126 is disposed on the upper housing 12, the at least one second arc-shaped plate 149 is disposed on the lower housing 14, and the at least one first arc-shaped plate 126 and the at least one second arc-shaped plate 149 are attached to the rotating body 28 from two sides of the rotating body 28, thereby limiting and guiding the rotating body 28.

In some embodiments, the at least one sensor assembly 20 further includes a detecting rod 24, the detecting rod 24 extends out of the housing 10 from the rotating body 28. A fourth limiting opening 1471 for allowing rotation of the detecting rod 24 is defined on the second bottom wall 147, a fifth limiting opening 1481 for allowing the rotation of the detecting rod 24 is defined on the second side wall 148, and the fifth limiting opening 1481 is communicated with the fourth limiting opening 1471.

The fourth limiting opening 1471 and the fifth limiting opening 1481 facilitate the rotation of the detecting rod 24 and define the rotating direction of the detecting rod 24. The upper housing 12 is not provided with the limiting opening, so that the detecting rod 24 only rotates toward the lower housing 14.

In some other embodiments, the upper housing 12 is provided with the limiting opening, and the detecting rod 24 is further rotatable toward the upper housing 12.

In some embodiments, the lower housing 14 includes the first bottom plate 142 and the first side plate 144, and the first side plate 144 is disposed around the edge of the first bottom plate 142 and is disposed at the one side, facing the upper housing 12, of the first bottom plate 142. That is, the first side plate 144 is disposed around the edge of the first bottom plate 142 and forms the groove structure with the first bottom plate 142. A part of the first side plate 144 is served as a part of the second side wall 148, that is, the second side wall 148 shares the part of the first side plate 144. The second side wall 148 includes a first sub-wall and a second sub-wall, the first sub-wall shares the first side plate 144, and the second sub-wall is disposed opposite to the first sub-wall. A first end of the at least one second arc-shaped plate 149 is connected to the second sub-wall, and a second end of the at least one second arc-shaped plate 149 extends into the first sub-wall and the second sub-wall. The first sub-wall is the arc-shaped structure matched with the rotating body 22. In some embodiments, the second side wall 148 and the first side plate 144 are spaced apart, and the first side plate 144 is correspondingly provided with the limiting opening. In some examples, the upper housing includes a second bottom plate and a second side plate. The second side plate is disposed around an edge of the second bottom plate and is disposed at the one side, facing the lower housing, of the second bottom plate. That is, the second side plate is disposed around the edge of the second bottom plate and forms a groove structure with the second bottom plate. A part of the second side plate is served as a part of the first side wall, that is, the first side wall shares the part of the second side plate. The first side wall includes a third sub-wall and a fourth sub-wall, the third sub-wall shares the second side plate, and the fourth sub-wall is disposed opposite to the third sub-wall. The at least one first arc-shaped plate extends from the third sub-wall to the fourth sub-wall. The first sub-wall is the arc-shaped structure adapted to the rotating body. In some embodiments, the first side wall and the second side plate are spaced apart, and the second side plate is correspondingly provided with the limiting opening.

Figure 11:
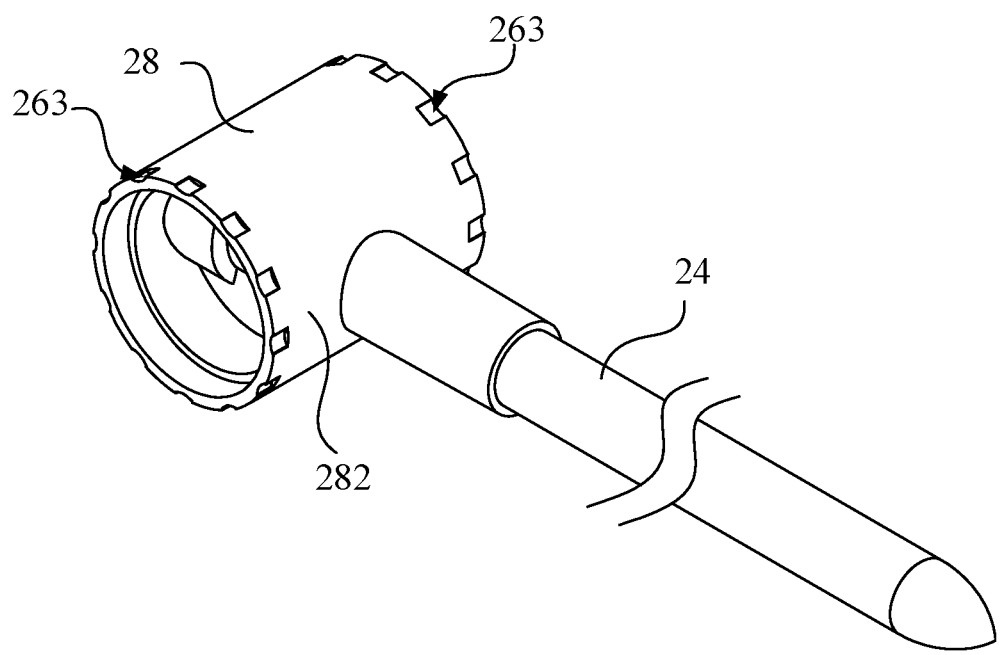
FIG. 11 is a structural schematic diagram of one sensor assembly of the soil testing device shown in FIG. 7.

Please refer to FIG. 11, FIG. 11 is a structural schematic diagram of one sensor assembly of the soil testing device shown in FIG. 7. The rotating body 28 includes a first side 282, the detecting rod 24 passes through the first side 282 of the rotating body 28 and is fixedly connected to the rotating body 28, which is convenient for connecting the detecting rod 24 and the rotating body 28. In some examples, the rotating body 28 further includes a second side disposed opposite to the first side 282, and the detecting rod 24 abuts against the second side and is connected to the second side, for example, the detecting rod 24 is connected to the second side of the rotating body 28 through an adhesive fixed connection manner, a hot-melt fixed connection manner, a snap-in connection manner, a threaded connection manner, etc. Certainly, the detecting rod 24 may also be connected to other structures of the rotating body 28.

In some embodiments, the soil testing device 1 includes the plurality of the sensor assemblies 20, each of the plurality of the sensor assemblies 20 includes one rotating body 28 and one detecting rod 24. In other embodiments, the soil testing device 1 includes the plurality of the sensor assemblies 20, and the plurality of the sensor assemblies 20 share one rotating body 28.

The soil testing device provided by the embodiments of the present disclosure is described in detail, and specific examples are used herein to describe the principles and embodiments of the present disclosure, and the above method and the core idea thereof; at the same time, for those who skilled in the art, according to the idea of the present disclosure, in a specific implementation manner and an application range, the content should be changed. In summary, the content of the present specification should not be construed as a limitation to the present disclosure.

What is claimed is:

1. A soil testing device, comprising:
    a housing; and
    at least one sensor assembly, rotatably connected to the housing; wherein,
    the at least one sensor assembly is configured to insert into soil and to output an electrical signal corresponding to a soil parameter to be displayed on a display unit; and
    wherein the at least one sensor assembly comprises at least one first limiting structure, the housing further comprises at least one second limiting structure, and the at least one first limiting structure is matched with the at least one second limiting structure, so as to limit the at least one sensor assembly in a predetermined position of the housing.

2. The soil testing device according to claim 1, wherein the at least one first limiting structure comprises an outer gear structure, the at least one second limiting structure comprises an inner gear structure corresponding to the outer gear structure, and the inner gear structure is engaged with the outer gear structure.

3. The soil testing device according to claim 2, wherein the at least one sensor assembly comprises a rotating portion and a detecting rod, the rotating portion is connected with the detecting rod, and the rotating portion is disposed in the housing, the detecting rod extends out of the housing from an interior of the housing; and
    the rotating portion comprises a base body and two protruding columns, the two protruding columns protrude from two sides of the base body in a direction perpendicular to an extending direction of the detecting rod, and the outer gear structure is disposed on a periphery of a corresponding one of the two protruding columns.

4. The soil testing device according to claim 3, wherein the housing comprises an upper housing, a lower housing, and a bracket; the upper housing is fixedly connected to the lower housing, the bracket is disposed between the upper housing and the lower housing, the bracket and the lower housing are spaced apart to form an accommodating space, and the rotating portion is disposed in the accommodating space and is capable of rotating in the accommodating space; and
    the bracket comprises at least one first cover portion, the at least one first cover portion covers on a part of the at least one first limiting structure, the inner gear structure is disposed at one side, facing the at least one first limiting structure, of the at least one first cover portion.

5. The soil testing device according to claim 4, wherein the bracket further comprises a second cover portion and a third cover portion, the second cover portion is connected with the third cover portion, the second cover portion covers on the base body, and the third cover portion covers on a part of the detecting rod; and
    two first cover portions are provided, the two first cover portions are disposed at two sides of the second cover portion in the direction perpendicular to the extending direction of the detecting rod.

6. The soil testing device according to claim 5, wherein the rotating portion further comprises two connecting columns, each of the two connecting columns is disposed between the base body and a corresponding one of the two protruding columns; and
    each of the two first cover portions comprises a first portion and a second portion connected with the first portion, a slit is defined between the first portion and the second portion, the first portion covers on the outer gear structure, and the second portion covers on a part of a corresponding one of the two connecting columns.

7. The soil testing device according to claim 6, wherein the lower housing comprises a first bottom plate and a first side plate, the first side plate is disposed around an edge of the first bottom plate and is disposed at one side, facing the upper housing, of the bottom plate; a first limiting opening for allowing rotation of the detecting rod is defined on the first side plate, a second limiting opening for allowing the rotation of the detecting rod is defined on the first bottom plate, and the first limiting opening is communicated with the second limiting opening.

8. The soil testing device according to claim 7, wherein the lower housing further comprises a baffle, the baffle is disposed at the one side, facing the upper housing, of the bottom plate; the baffle is disposed around the rotating portion and forms an accommodating groove with the bottom plate for accommodating the rotating portion; a third limiting opening for allowing the rotation of the detecting rod is defined on the baffle, the third limiting opening, the second limiting opening, and the first limiting opening are communicated.

9. The soil testing device according to claim 8, wherein the bracket covers on the rotating portion and is fixedly connected to the baffle, so as to limit the rotating portion between the bracket and the lower housing.

10. The soil testing device according to claim 4, wherein the soil testing device further comprises a circuit board, the circuit board is disposed at one side of the bracket facing away from the lower housing; and a first through hole is defined on the bracket, at least one wire passes through the first through hole, and the circuit board is electrically connected to the at least one sensor assembly through the at least one wire.

11. The soil testing device according to claim 1, wherein a rotating space is defined in the housing, the at least one sensor assembly comprises a rotating body, the rotating body is columnar and is disposed in the rotating space, and the rotating body is capable of rotating in the rotating space;

the at least one first limiting structure comprises limiting notches, the limiting notches are defined on an outer peripheral surface of the rotating body and defined around a circumference of the rotating body; and the at least one second limiting structure comprises at least one limiting protrusion block, the at least one limiting protrusion block is disposed on the housing, and the at least one limiting protrusion block is configured to engage with a corresponding one of the limiting notches, so as to limit the rotating body.

12. The soil testing device according to claim 11, wherein the housing comprises an upper housing and a lower housing, at least one first limiting groove is defined at one side, facing the lower housing, of the upper housing, at least one second limiting groove is defined at one side, facing the upper housing, of the lower housing, and the at least one first limiting groove and the at least one second limiting groove are disposed opposite to each other and form the rotating space.

13. The soil testing device according to claim 12, wherein the upper housing comprises a first bottom wall and a first side wall, the first bottom wall and the first side wall form the at least one first limiting groove; and the upper housing further comprises at least one first arc-shaped plate, the at least one first arc-shaped plate is disposed on the first bottom wall and is connected to the first side wall; one side, away from the first bottom wall, of the at least one first arc-shaped plate is an arc-shaped structure matched with the rotating body.

14. The soil testing device according to claim 13, wherein the at least one limiting protrusion block is disposed on the at least one first arc-shaped plate.

15. The soil testing device according to claim 12, wherein the lower housing comprises a second bottom wall and a second side wall, the second bottom wall and the second side wall form the at least one second limiting groove; the lower housing further comprises at least one second arc-shaped plate, the at least one second arc-shaped plate is disposed on the second bottom wall and is connected to the second side wall; one side, away from the second bottom wall, of the at least one second arc-shaped plate is an arc-shaped structure matched with the rotating body.

16. The soil testing device according to claim 15, wherein the at least one limiting protrusion block is disposed on the second bottom wall and is adjacent to the at least one second arc-shaped plate.

17. The soil testing device according to claim 15, wherein the at least one sensor assembly further comprises a detecting rod, the detecting rod extends out of the housing from the rotating body; and a fourth limiting opening for allowing rotation of the detecting rod is defined on the second bottom wall, a fifth limiting opening for allowing the rotation of the detecting rod is defined on the second side wall, and the fifth limiting opening is communicated with the fourth limiting opening.

18. The soil testing device according to claim 17, wherein the rotating body comprises a first side, the detecting rod passes through the first side of the rotating body and is fixedly connected to the rotating body.

* * * * *